United States Patent
De Franciscis et al.

(10) Patent No.: US 12,428,644 B2
(45) Date of Patent: Sep. 30, 2025

(54) CA-IX APTAMERS AND DIAGNOSTIC AND THERAPEUTIC USES THEREOF

(71) Applicant: BRACCO IMAGING S.P.A., Milan (IT)

(72) Inventors: Vittorio De Franciscis, Naples (IT); Carla Lucia Esposito, Naples (IT); Silvia Catuogno, Naples (IT); Silvia Nuzzo, Salerno (IT); Alessandro Maiocchi, Monza (IT); Margherita Iaboni, Qualiano (IT); Aldo Di Vito, Naples (IT); Erika Reitano, Banchette (IT); Luisa Poggi, Banchette d'Ivrea (IT)

(73) Assignee: BRACCO IMAGING S.P.A., Milan (IT)

( * ) Notice: Subject to any disclaimer, the term of this patent is extended or adjusted under 35 U.S.C. 154(b) by 870 days.

(21) Appl. No.: 17/642,753

(22) PCT Filed: Sep. 16, 2020

(86) PCT No.: PCT/EP2020/075806
§ 371 (c)(1),
(2) Date: Mar. 14, 2022

(87) PCT Pub. No.: WO2021/052982
PCT Pub. Date: Mar. 25, 2021

(65) Prior Publication Data
US 2022/0348923 A1 Nov. 3, 2022

(30) Foreign Application Priority Data
Sep. 16, 2019 (EP) .................................... 19197506

(51) Int. Cl.
C12Q 1/6886 (2018.01)
A61K 45/06 (2006.01)
C12N 15/115 (2010.01)

(52) U.S. Cl.
CPC ............ *C12N 15/115* (2013.01); *A61K 45/06* (2013.01); *C12Q 1/6886* (2013.01); *C12N 2310/16* (2013.01); *C12N 2310/3517* (2013.01)

(58) Field of Classification Search
None
See application file for complete search history.

(56) References Cited

FOREIGN PATENT DOCUMENTS

| | | |
|---|---|---|
| CN | 107648620 A | 2/2018 |
| WO | 2011139375 A1 | 11/2011 |
| WO | 2012027493 A1 | 3/2012 |
| WO | 2014128258 A1 | 8/2014 |
| WO | 2017181163 A2 | 10/2017 |

OTHER PUBLICATIONS

Catuogno, S., et al., "Developing Aptamers by Cell-Based SELEX," Methods Mol. Biol., 1380:33-46 (2016).
Ellington, A., et al., "In vitro selection of RNA molecules that bind specific ligands," Nature, 346:818-822 (1990).
Gao, S., et al., "Post-SELEX optimization of aptamers," Anal. Bioanal. Chem., 408(17):4567-4573 (2016).
Gopinath, S.C., et al., "An RNA aptamer that distinguishes between closely related human influenza viruses and Inhibits haemagglutinin-mediated membrane fusion," J. Gen. Virol., 87:479-487 (2006).
International Search Report and Written Opinion for PCT/EP2020/075806, mailed Dec. 2, 2020.
Levy-Nissenbaum, E. et al., "Nanotechnology and aptamers: applications in drug delivery," Trends Biotechnol. 26 (8):442-449 (2008).
Radom, F., et al., "Aptamers: molecules of great potential," Biotechnol. Adv., 31:1260-1274 (2013).
Song, K.M., et al., "Aptamers and Their Biological Applications," Sensors, 12:612-631 (2012).
Stoltenburg, R., et al., "SELEX-A (r)evolutionary method to generate high-affinity nucleic acid ligands," Biomol. Eng., 24:381-403 (2007).
Tuerk, C., et al., "Systematic evolution of ligands by exponential enrichment: RNA ligands to bacteriophage T4 DNA polymerase," Science, 249:505-510 (1990).
Wykoff, C., et al., "Hypoxia-inducible Expression of Tumor-associated Carbonic Anhydrases," Cancer Res., 60:7075-7083 (2000).
Zhu, L., et al., "CAIX aptamer-functionalized targeted nanobubbles for ultrasound molecular imaging of various tumors," Int. J. Nanomedicine, 13:6481-6495 (2018).
Hasegawa, H., "Improvement of aptamer affinities through multimerization," Section 1-4-2, pp. 10-11 (2017).
Miyakawa, S., et al., "Structural and molecular basis for hyperspecificity of RNA aptamer to human immunoglobulin G," RNA, 14(6) 1154-1163 (2008).
Tan, L., et al., "Designer tridentate mucin 1 aptamerfor targeted drug delivery," Journal of Pharmaceutical Sciences, 101:1672-1677 (2012).
Ulrich, H., et al., "RNA and DNA aptamers in cytomics analysis," Cytometry Part A, 59A:220-231 (2004).

*Primary Examiner* — Katherine D Salmon
(74) *Attorney, Agent, or Firm* — VIVICAR Law, PLLC

(57) ABSTRACT

The present invention provides nucleic acid aptamers binding to the Carbonic Anhydrase IX (CA-IX) enzyme, derivatives and conjugates thereof and their use as diagnostic tools, particularly for the imaging of organs and tissues expressing CA-IX, or as therapeutic agents for prevention or treatment of CA-IX related diseases.

17 Claims, 3 Drawing Sheets
Specification includes a Sequence Listing.

CA-IX APTAMERS AND DIAGNOSTIC AND THERAPEUTIC USES THEREOF

CROSS-REFERENCE TO RELATED APPLICATIONS

This application is the national stage application of corresponding international application number PCT/EP2020/075806, filed Sep. 16, 2020, which claims priority to and the benefit of European application no. 19197506.9, filed Sep. 16, 2019, which is hereby incorporated by reference in its entirety.

The present invention provides nucleic acid aptamers binding to the Carbonic Anhydrase IX (CA-IX), derivatives and conjugates thereof and their use as diagnostic tools, particularly for the imaging of organs and tissues expressing CA-IX, or as therapeutic agents for prevention or treatment of CA-IX related diseases.

BACKGROUND

Aptamers

Recently, functional oligonucleotide-based biomolecules, called aptamers, have attracted great interest as potential alternatives to antibodies. The technology of aptamer selection has been drawn to the attention of the scientific community due to its applicability in diagnosis and treatment of diseases.

The oligonucleotide aptamers range in size from about 20 to about 80 bases (8 to 25 kDa) and their structures are responsible for intramolecular interactions (Levy-Nissenbaum E. et al., *Trends Biotechnol.* 2008, 26(8), 442-449). Aptamers bind to their targets by interactions between aromatic compounds, base pairings by hydrogen ligation, van der Waals interactions, and electrostatic interactions between charged groups or hydrogen bonds. In consequence, aptamers undergo conformational changes after target recognition and biomolecular interaction.

These biological, physical and chemical properties make these oligonucleotides effective recognition tools for diagnosis and therapy. The application of aptamers in biological fields is mainly limited due to their degradation by ribozymes. Chemical modifications are required in order to protect them against nucleases, improving their thermal stability and their pharmacokinetic properties.

Among the modifications, the exchange of the OH at the 2'-position of the ribose by 2'-F or 2'-$NH_2$ groups can be performed to improve aptamer stability in the cellular environment. Other alterations of aptamers can include terminal capping with small molecules such as amine, a phosphate group, or residue of thymidine and other non-natural bases (Gao S. et al, *Anal. Bioanal. Chem.* 2016, 408(17), 4567-4573).

The aptamers are selected by an in vitro process through the Systematic Evolution of Ligands by EXponential enrichment (SELEX). This method was concomitantly described by Tuerk and Gold (*Science*, 1990, 249, 505-510) and Ellington and Szostak (*Nature*, 1990, 346, 818-822). SELEX method involves the progressive selection of aptamers by the repetition of binding cycles, elution, and amplification of ligands from a random nucleic acid library, to select sequences with a higher binding affinity for a selected target.

A new application of this technology, called "cell-SELEX" has been developed allowing the selection of aptamers that bind to specific target cells (de Franciscis V. et al., *Methods Mol Biol.*, 2016, 1380, 33-46). The selection parameters can be easily manipulated to obtain more efficient aptamers for a wide range of conditions (e.g. pH, temperature or buffer composition) (Radom F. et al, *Biotechnol. Adv.* 2013, 31(8), 1260-1274). Some modifications have been included in the traditional SELEX method, such as affinity chromatography, capillary electrophoresis and filtration membranes, to maximize affinity and specificity and to improve the selection speed and success rate of the specific aptamers (Stoltenburg R et al, *Biomol. Eng.* 2007, 24(4), 381-403). The characteristics of the selected oligonucleotides are identified using various physical, chemical and biological assays (Song K M et al, *Sensors,* 2012, 12(1), 612-631). Once selected, they can be synthesized in great quantity with precision and reproducibility by chemical reactions. These chemical processes are more cost-effective than the production of antibodies.

When compared to antibodies, the aptamers have a relatively small size, which facilitates their chemical synthesis and possible modifications. They are biocompatible and poorly immunogenic in vivo. They have high selectivity and the ability to bind and recognize specific targets, presenting an affinity constant (Kd) in the nanomolar range, lower than the antibodies, generally having a Kd in the milli/micromolar range. Also, they penetrate tissues faster and more efficiently because of their significantly lower molecular weight and can distinguish extracellular or intracellular domains of proteins, which cannot be differentiated by antibodies (Gopinath S. C. et al, *J. Gen. Virol.,* 2006, 87(3), 479-487).

The strong target affinity/selectivity, cost-effectivity, chemical versatility and safety of aptamers are superior also to traditional peptide- or protein-based ligands, which make them particularly suitable for molecular imaging. In fact, aptamers are amendable to chemical modification for a long-term stability and to bioconjugation to various moieties and are therefore considered to be extremely useful as specific imaging agents (e.g. for optical, magnetic resonance, nuclear, computed tomography, ultrasound and multimodality imaging), as well as therapeutics agents.

CA-IX

Carbonic anhydrase IX (CA-IX) is a zinc metalloenzyme located on the surface of the cells. It is a member of the large carbonic anhydrases (CAs) family of enzymes catalysing the reversible conversion of carbonic dioxide to protons and bicarbonate, leading to a decrease in pH.

To date, 16 CA isoforms have been characterized in mammals, which differ in their cellular localization, catalytic activity, susceptibility to different inhibitors and tissue-specific distribution.

Among them, CA-IX is a marker of the hypoxic response in tumors, because its gene expression is promoted by the master regulator of hypoxia, named Hypoxia Inducible Factor 1 (HIF-1), believed to be involved in maintaining the acidic environment of hypoxic cells (Wykoff et al., *Cancer Res.* 2000, 60, 7075-7083). Tumor hypoxia, mostly resulting from poor perfusion and anemia, is one of the key factors in inducing the development of cell clones with an aggressive and treatment-resistant phenotype that leads to rapid progression and poor prognosis in several cancer types. Cancer cells, in fact, survive in a hostile environment changing their gene expression, in particular that of genes involved in pH control.

CA-IX plays an important role in the growth and metastasis of numerous tumors (including renal cancer, cervical cancer, colon cancer, prostate cancer, breast cancer, head and neck tumors, etc.) because its catalytic activity contributes to the reduction of the extracellular pH (pHe) producing an acid microenvironment which increases cancer cell proliferation and invasion.

Unlike other CAs, many studies have demonstrated that CA-IX is expressed only in few normal tissues (namely the intestinal and stomach mucosa, gallbladder and testis), whereas it becomes overexpressed in many types of cancer cells. Therefore, CA-IX targeting using specific tools opens new important fields to improve the conventional therapies and the early diagnosis and prognosis of malignant tumors.

The main issue faced in the selection of CA-IX targeting moieties, and in particular of anti-CA-IX aptamers, concerns how specifically targeting CA-IX in its active state.

The classes of CA-IX-targeting agents developed so far, for both imaging and/or therapeutic applications, include monoclonal antibodies (e.g. G250, M75) or mini-antibodies (e.g. A3 and CC7) and small chemical compounds, such as inorganic ions, sulfonamide based compounds, phenols and coumarins. Some of these agents are currently under clinical development.

In particular, the monoclonal antibodies (mab) M75 and G250 represent the first solutions developed to target CA-IX enzyme. Mab M75 binds to CA-IX's proteoglycan-like (PG-like) domain on the N-terminus of the target, whereas mab G250 interacts with CA-IX's catalytic domain. A chimeric version of G250 (designated cG250) labeled with the radionuclide $^{124}$I was developed for the detection of clear cell Renal Cell Carcinoma (ccRCC).

Although, typically, monoclonal antibodies have been considered as the ligands of choice for most tumor targeting applications, it is becoming increasingly clear that they are subjected to many disadvantages. In fact, antibodies are characterized by slow and inefficient tumor penetration and long blood residence which requires the use of long-lived radioisotopes and imaging at late time points, exposing patients to a high radiation burden. Indeed, $^{124}$I-cG250 reaches tumor/blood ratios suitable for imaging only 2-7 days after injection into the patient. Additionally, monoclonal antibodies may be immunogenic precluding repeated administration for routine diagnostic procedures.

These problems could be circumvented with the use of small molecules. Unlike large macromolecules, small molecules clear rapidly from circulation and thus reach tumor/blood ratios suitable for imaging at early time-points. This in turn allows physicians to obtain diagnostic information much more quickly than with antibody-based imaging agents.

Among small chemical compounds targeting CA-IX, the best investigated and most robust class of inhibitors are the sulfonamides due to their high affinity, availability, and ease of chemical manipulation. However, despite some of them being promising agents, concerns remain about off-target toxicities due to interactions with intracellular CAs, and other extracellular CAs such as CA-XII, which is expressed in tumors but also in normal tissues.

WO2014/128258 describes a CA-IX targeting compound, e.g. the antibody cG250, for use in the treatment of cancer and a method for diagnosing, predicting and/or classifying a cancer disease comprising quantifying CA-IX expression and determinating a CA-IX score.

WO2011/139375 discloses novel antibodies and fragments thereof binding CA-IX and useful in diagnosis and therapy of cancer diseases associated with hypoxia and/or elevated CA-IX activity. CN107648620 and Zhu L. et al, Int. J. Nanomedicine, 2018, 13, 6481-6495 disclose targeted ultrasonic nanobubbles carrying a CA-IX aptamer immobilized in the outer shell of the lipid monolayer of the nanoparticle; such compounds can penetrate the tumor vasculature and be used for ultrasound molecular imaging of tumor parenchymal cells.

WO2012/027493 describes a non-invasive method for detecting cancer cells in vivo by administering to a subject one or more targeted imaging probes, specifically binding a target selected from CA-IX, CA-XII and others. Aptamers are mentioned among the possible targeted probes, even though no examples of specific isolated oligonucleotides are reported.

Despite the efforts, there is still the need to develop CA-IX binding agents, characterized by a high and specific affinity for the target, to be used in diagnosis and/or therapy.

SUMMARY

The present invention is based on the identification of RNA aptamer sequences specifically targeting Carbonic Anhydrase IX (CA-IX) enzyme with high affinity.

Considering the up-regulation of CA-IX in many types of cancer as marker of hypoxia, the anti-CA-IX aptamers of the invention may be useful for an early cancer diagnosis and staging in the perspective of more effective therapeutic treatments, and to detect and follow the response of disseminated metastatic disease to systemic and targeted therapies.

In particular, the aptamers of the invention solve the problem of specifically recognize the target at the site where it is physiologically present, i.e. on the cell surface where CA-IX is expressed, thus demonstrating to be suitable for their use in vivo. In fact, the aptamers herein described have been found able to bind directly the cells overexpressing CA-IX on their surface.

To that purpose, a cell-SELEX approach has been applied for the specific selection of aptamers binding CA-IX expressed on the cell surface.

DETAILED DESCRIPTION

A library of RNA molecules modified with 2'-fluoro pyrimidines was assayed for the binding to COS7 cells transiently transfected with human CA-IX (COS7-CAIX). The selection process involved repeated cycles of: 1. Incubation of the aptamer library on COS7 cells for the couter selection step; 2. Recovering of the unbound sequences and incubation on COS7-CAIX cells for the selection step; 3. Recovering of the bound sequences and amplification. Following repeated selection steps, the final pool of RNA molecules was cloned, individual sequences showing highest COS7-CA-IX binding were isolated and their sequence and affinity for the target was determined.

In a first aspect, the invention provides two aptamers able to bind to Carbonic Anhydrase IX (CA-IX) and comprising a RNA sequence selected from UCGAAUGAACCAAG-GUUCCUCGGC (SEQ ID NO: 1) and UUCGUGCC-GCUGAGUGCGUACGGGC (SEQ ID NO: 2) or their derivatives thereof.

In one embodiment, the above aptamers have a length of up to 100 nucleotides.

Specific RNA sequences, corresponding to SEQ ID NO: 1 or SEQ ID NO: 2, of 24 and 25 nucleotides respectively, were obtained by shortening two originally selected 84mer aptamers in order to obtain small sequences useful for imaging and therapeutic applications.

In a preferred embodiment the RNA aptamers defined above are characterized by being nuclease-resistant. In a more preferred embodiment the RNA aptamers defined above are characterized by having all the pyrimidine residues modified with 2'-F (fluoropyrimidines).

In another more preferred embodiment the RNA aptamers defined above can be bound to a binding moiety, such as biotin.

Preferred aptamers of the invention consists of SEQ ID NO: 1 or SEQ ID NO: 2. More preferred is aptamer consisting of SEQ ID NO: 1.

Aptamers Modification

Aptamers of the invention can be modified, e.g. to increase their resistance to nucleases, to modulate their pharmacokinetics, or to be conjugated with diagnostic or therapeutic moieties.

Preferably, the RNA aptamer of the invention has at least one or all of the pyrimidine residues modified with 2'-fluoro. Furthermore, its modification may include a chemical substitution at a position preferably selected from the group consisting of a sugar position, a phosphate position and a base position of the nucleic acid. In some embodiments, the modification is selected from the group consisting of: biotinylation, incorporation of a fluorescent label, incorporation of a modified nucleotide, 2'-pyrimidine modification, 3'-position capping, conjugation to a linker, conjugation to a compound or a drug, conjugation to a cytotoxic moiety, and labeling with a fluorophore, a radioisotope, an ultrasound contrast agent or a reporter moiety. The position of the modification can be varied depending on the type of moiety that is attached to the aptamer. For instance, the aptamer sequences can be modified at the 3'-terminus and/or at the 5'-terminus.

In a preferred embodiment the aptamers are linked to biotin, e.g. biotinylated at the 3'-terminus, as shown in the following formula (I)

produce contrast or signal using optical imaging; magnetic moieties, including a chelating agent for magnetic resonance agents which is able to form stable complexes with paramagnetic metal ions; radiolabel moieties; X-ray moieties that may be used to produce contrast or signal using X-ray imaging, such as iodinated organic molecules or chelates of heavy metal ions; ultrasound imaging moieties that may be used to produce contrast or signal using ultrasound targeted microbubbles; and photoacoustic imaging moieties, including photoacoustic imaging-compatible agents.

The aptamer and the reporter moiety or label may be linked either covalently or noncovalently, optionally by interposition of a suitable linker or spacer, including peptides, amino acids or nucleic acids. Furthermore, the aptamer and the reporter moiety or label may be linked using a tag system, including biotin/avidin, biotin/streptavidin, biotin/NeutrAvidin, or digoxigenin (DIG) systems.

In a further aspect, the invention provides a composition comprising at least one aptamer as herein defined and one or more suitable pharmaceutically acceptable carriers, excipients, diluents and/or additives. The ingredients of the composition can be varied depending on the intended use, whether for diagnostic, therapeutic or imaging applications. For instance, the composition can further contain one or more therapeutic compounds and/or one or more imaging agents.

In one embodiment, the composition is used for the imaging of a target tissue bearing CA-IX and comprises an aptamer conjugated or labeled with a reporter moiety as above defined. The composition can be e.g. in the form of a liposome or nanoparticles and can be suitable for different types of administration. In one embodiment the composition

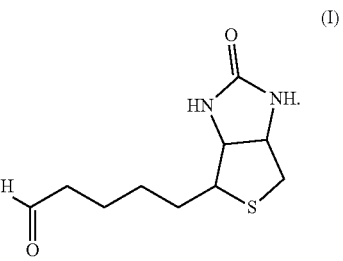

(I)

The aptamers of the invention, suitably labeled or conjugated with reporter or therapeutic moieties, can be used in the diagnosis, therapy or visualization of CA-IX-related states, disorders, dysfunctions, conditions or diseases, particularly cancer diseases. Exemplary applications include the diagnosis or therapy of a cancer disease correlated with the expression of CA-IX, such as for instance renal cancer, cervical cancer, colon cancer, prostate cancer, breast cancer and head and neck tumor, and of heart failure.

In a particular embodiment of invention, the aptamers labeled with a reporter moiety can be used in the imaging of body tissues or organ systems expressing CA-IX and particularly tumor parenchymal tissue.

Suitable imaging techniques include magnetic resonance imaging, positron-emission tomography (PET), computed tomography (CT), ultrasound, photoacoustic imaging (PAI), near-infrared fluorescence (NIRF), single photon emission computed tomography (SPECT).

For imaging applications, the reporter moiety linked to the aptamer is generally selected from: molecules capable of generating a fluorescent signal, such as fluorescein; FITC; Alexa dyes; Cy dyes; DyLight dyes; IRDye dyes or VivoTag dyes; optical moieties, including agents that may be used to is suitable for parenteral administration, preferably for intravenous or subcutaneous administration. Said composition can be used for visualizing CA-IX expressing tissues or organs, such as tumor parenchymal tissue.

A kit is also provided that contains at least one aptamer of the invention, preferably labeled or conjugated with reporter or therapeutic moiety in one or more containers.

BRIEF DESCRIPTION OF THE SEQUENCE LISTING

SEQ ID NO: 1 sets out a short aptamer sequence of the 24 nt named SAM-2.T1:

5'-UCGAAUGAACCAAGGUUCCUCGGC-3';

SEQ ID NO: 2 sets out a short aptamer sequence of the 25 nt named SAM-1.T1:

5'-UUCGUGCCGCUGAGUGCGUACGGGC-3'.

EXPERIMENTAL SECTION

Equipment

Figure 1:
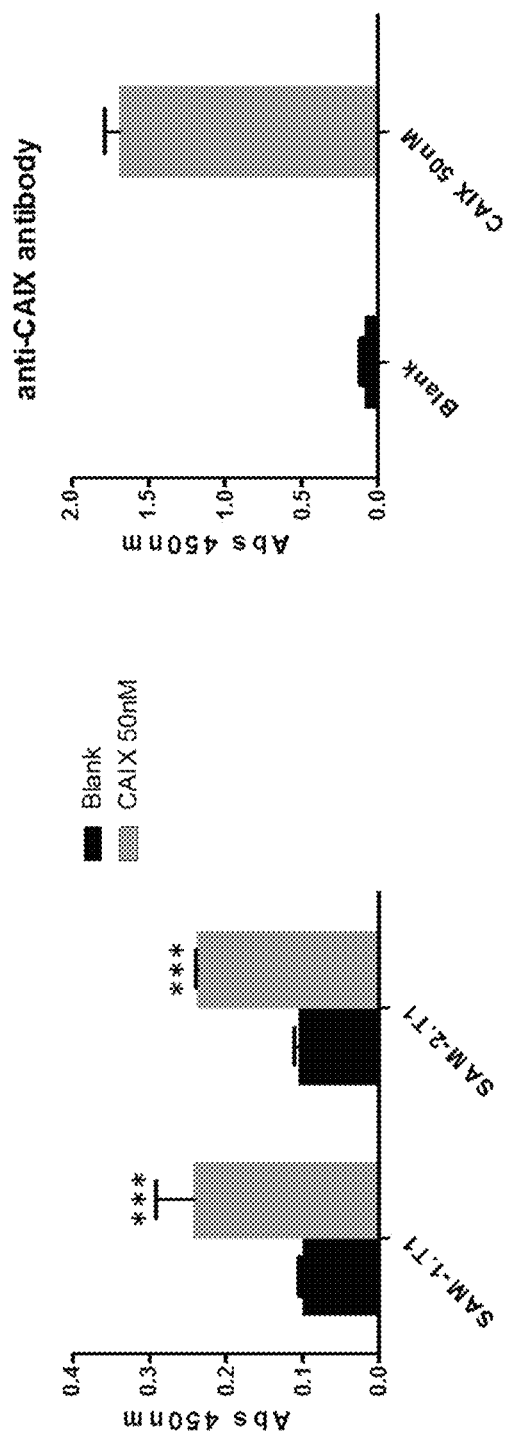
FIG. 1: Binding evaluation on CA-IX purified protein by ELONA assay. Absorbance at 450 nm for SAM-1.T1 and SAM-2.T1 (in the left panel) and polyclonal antibody anti-HSA (in the right panel).

RT-qPCR was carried out by StepOne™ Plus Real-Time PCR System (Applied Biosystems). Gel visualization was performed with Gel Doc EZ System (Bio-Rad). ELONA data were acquired by Multiskan™ FC Microplate Photometer (ThermoFisher Scientific).

List of Abbreviations
CA-IX Carbonic Anhydrase IX
SELEX Systematic Evolution of Ligands by Exponential enrichment
RNA Ribonucleic acid
DNA Deoxyribonucleic acid
DMF Dimethylformamide
DMSO Dimethyl sulfoxide
WT Wild type
nt nucleotides
2'-F-Py 2'-Fluoro pyrimidine
PAGE PolyAcrylamide gel Electrophoresis
pHe Extracellular pH
PG Proteoglycan-like domain
HPLC High Performance Liquid Chromatography
HSA Human serum albumin
ELONA Enzyme-linked oligonucleotide assay
HIF-1 Hypoxia Inducible Factor 1
MES 2-(N-morpholino)ethanesulfonic acid
COS7 CV-1 (simian) in Origin with SV40 genetic material cells
Rt-q PCR Real-time polymerase chain reaction

Example 1: Selection and Preparation of Anti-CA-IX Aptamers

Selection: RNA sequences against CA-IX were screened from a non-naïve library of 84 nt fragments by following a cell-SELEX approach. The method included cycles of counter-selection/selection steps of a pre-enriched pool of aptamers with affinity for CAs on COS7-WT and transiently transfected COS7-CA-IX cells respectively, in which at each round a selective pressure was generated. The enriched pool was incubated on cells in acid condition (in the presence of 60 mM MES buffer) in order to reach the extracellular pH maintained by CA-IX (around 6.8). Before each round of cell-SELEX, the pool was transcribed using a mutant form of T7 RNA polymerase able to incorporate 2'-fluoro pyrimidines in the RNA sequences. The counter-selection step was performed against COS7-WT cells to avoid the selection of aptamers that recognize proteins normally expressed on COS7 cells. The selection step was performed against transient transfected COS7-CA-IX cells in order to select aptamers specific for the target. For each cycle, the pool of 2'-fluoro pyrimidines RNA sequences was firstly incubated on the COS7-WT cells at 37° C., then unbound 2'-fluoro pyrimidines RNA sequences were incubated on COS7-CA-IX cells. After several washes, the sequences were recovered by total RNA extraction. At the end of cell-SELEX protocol, the last cycle was cloned and the samples were sequenced. The resulting sequences were analyzed for enrichment and binding assays by RT-qPCR were performed in order to select the sequences able to bind COS7-CA-IX cells. Essentially, DNA sequences were amplified and transcribed, then RNA sequences were incubated at 100 nM, as final concentration, for 15 minutes at 37° C., after pre-treatment with yeast tRNA 200 μg/mL, on COS7-WT cells and COS7-CA-IX cells in acid condition. Following incubation, cells were washed 3 times with PBS and recovered in TRIsure reagent. An RNA sequence used as reference control was spotted in each point for the normalization. A fold ratio was calculated comparing binding values of COS7-CA-IX over COS7-WT cells. Six sequences representatives of couples or groups of identical sequences were screened. Those with higher fold ratio were chosen for further analysis, performing experimental triplicates. In order to obtain shorter sequences useful for imaging applications, the 84mer original molecules were truncated, selecting the shorter sequences corresponding to SEQ ID NO: 1 (SAM-2.T1) and SEQ ID NO: 2 (SAM-1.T1), by isolating the more structured region and checking that each short sequence maintained the folding of the corresponding portion in the long aptamer. The retention of the binding capability in the truncated sequences was assessed in the following example 2.

Preparation: The selected aptamers of the invention were then obtained by artificial synthesis. For instance, they were generated synthetically by solid phase synthesis with a RNA synthesizer, according to methods well known in the art. They were, then, conjugated to Biotin at the 3'-end of the sequence.

The RNA sequences were conjugated at their 3'-end to the commercial Biotin after insertion of a $C_6$-amino linker (3'-$C_6$—$NH_2$). The linker was inserted at the 3'-terminal phosphate by condensation with a $C_6$ aliphatic diamine in basic catalysis. The resulting free $NH_2$ moiety was coupled with Biotin-NHS ester, to form a covalent amide bond. The Biotin-NHS ester was dissolved in high-quality anhydrous DMF or DMSO, and the reaction was carried out in 0.1-0.2 M sodium bicarbonate buffer, pH 8.3, at room temperature. Purification was performed by PAGE followed by HPLC.

Example 2: Binding and Affinity of Aptamers SAM-1.T1 and SAM-2.T1 to CA-IX Positive Cells To the aim of confirming that the short aptamers SAM-1.T1 (SEQ ID NO: 2) and SAM-2.T1 (SEQ ID NO: 1) contained the active site of the original molecules and preserved high binding and affinity to COS7-CA-IX cells, binding assays were performed in duplicate comparing the sequences binding capability on COS7-CA-IX over COS7-WT cells. The COS7 cells were seeded and transfected with human CA-IX cDNA. After 24 h, the RNA sequences were incubated at 100 nM, as final concentration, for 15 minutes at 37° C. on COS7-WT and COS7-CA-IX in acid conditions. Samples were analysed by RT-qPCR to quantify the amount of bound aptamers and the fold change over COS7-WT cells was calculated.

The fold change value of 1.3 and 2.4 was obtained for aptamers SAM-1.T1 and SAM-2.T1 respectively. This result confirmed their ability to bind the target CA-IX in its physiological conformation on the membrane of the cell surface.

Example 3: Binding Assay of Aptamers SAM-1.T1 and SAM-2.T1 to Human CA-IX Purified Protein The binding of aptamers SAM-1.T1 (SEQ ID NO: 2) and SAM-2.T1 (SEQ ID NO: 1) was further investigated in a different experiment. Biotinylated aptamers SAM-1.T1 and SAM-2.T1 were tested on human CA-IX purified protein to confirm their ability to recognize the target.

Sequences SAM-1.T1 and SAM-2.T1 200 nM, biotinylated at the 3'-terminus, were incubated on 96 well microtiter high binding plates previously coated or non-coated (blank) with 50 nM human CA-IX purified protein. For each experiment an anti-CA-IX antibody was used as positive control. Samples were then analyzed by ELONA assay. Results, shown in FIG. 1, indicated that both the aptamers bind to CA-IX human protein as the anti-CA-IX antibody.

Example 4: Aptamers SAM-1.T1 and SAM-2.T1 Stability in Human Serum

Aptamers SAM-1.T1 and SAM-2.T1 were tested for stability in human serum in order to evaluate their resistance to enzymatic degradation. They were incubated in 87% human serum at 37° C. The experiment was performed in triplicate. The samples were collected at different times (T0, 1, 2, 4, 8, 12, 24, 48, 72 h), incubated with proteinase K for 1 h at 37° C. in order to degrade serum proteins and loaded on a denaturing gel.

Figure 2:
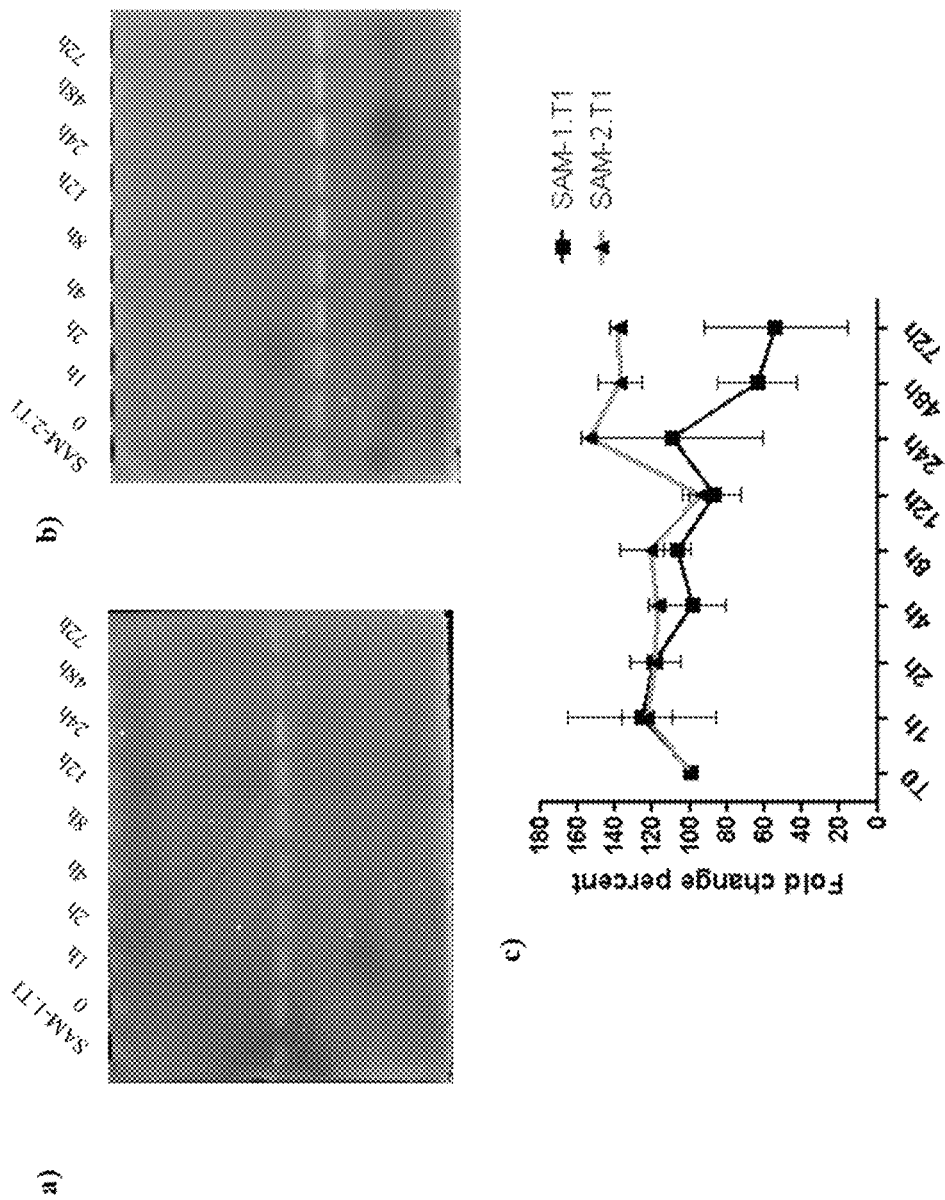
FIG. 2: SAM-1.T1 and SAM-2.T1 aptamers stability in human serum: a) SAM-1.T1 and b) SAM-2.T1 samples collected at different times were loaded on a denaturing gel (upper panel) and c) bands were quantified by ImageJ program (lower panel). The first line for both gels indicates the sequence not treated with human serum to assess the right size of the samples.

Results, reported in FIG. 2, showed that SAM-1.T1 and SAM-2.T1 aptamers are extremely stable in human serum; in particular, SAM-1.T1 aptamer was stable until 24 hours and SAM-2.T1 aptamer was stable for more than 72 hours.

Example 5: Binding Affinity of Aptamers SAM-1.T1 and SAM-2.T1 to HSA

Figure 3:
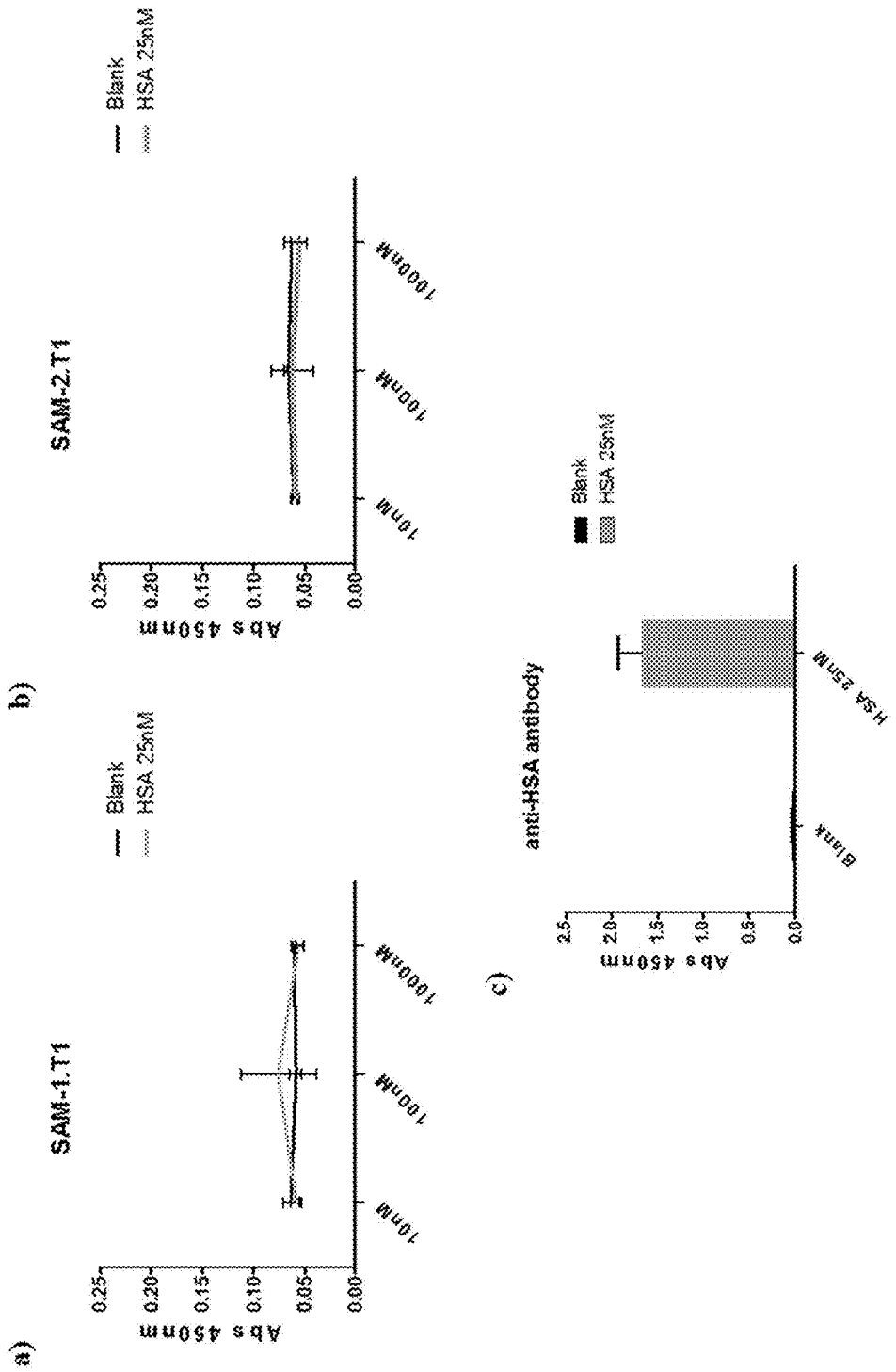
FIG. 3: $K_d$ evaluation for HSA by ELONA assay. Absorbance at 450 nm for (a) SAM-1.T1, (b) SAM-2.T1 and (c) anti-HSA polyclonal antibody.

The ELONA assay was performed in order to evaluate the binding of SAM-1.T1 and SAM-2.T1 aptamers to human serum albumin (HSA). Biotinylated SAM-1.T1 and SAM-2.T1 aptamers were incubated at increasing concentrations (10-100-1000 nM) on 96 well microtiter high binding plates previously coated or not-coated (blank) with 25 nM HSA. No aptamer binding was detected in any of the conditions used, indicating that SAM-1.T1 and SAM-2.T1 aptamers do not react with HSA up to 1000 nM. In each experiment an anti-HSA biotinylated polyclonal antibody was used as positive control. The results are shown in FIG. 3.

The invention claimed is:

1. A RNA aptamer that specifically binds to Carbonic Anhydrase IX enzyme (CA-IX), containing SEQ ID NO: 1 or SEQ ID NO: 2.

2. The aptamer according to claim 1, characterized in that it has a length of up to 100 nucleotides.

3. The aptamer according to claim 1, consisting of SEQ ID NO: 1.

4. The aptamer according to claim 1, consisting of SEQ ID NO: 2.

5. The aptamer according to claim 1, wherein all the pyrimidine residues are modified to 2'-fluoropyrimidines.

6. The aptamer according to claim 5 which is further modified to comprise at least one chemical modification, wherein said modification is a chemical substitution at a position selected from a sugar position, a phosphate position and a base position of the nucleic acid.

7. The aptamer according to claim 6, wherein said modification is selected from the group consisting of incorporation of a modified nucleotide, conjugation to a compound and labelling with a reporter moiety.

8. The aptamer according to claim 7, wherein the reporter moiety is selected from the group consisting of a fluorophore moiety, a magnetic or paramagnetic moiety, a radiolabel moiety, an affinity label, an X-ray moiety, an ultrasound imaging moiety, a photoacoustic imaging moiety and a nanoparticle-based moiety.

9. The aptamer according to claim 8, wherein the affinity label is biotin.

10. The aptamer according to claim 2, wherein all the pyrimidine residues are modified to 2'-fluoropyrimidines.

11. The aptamer according to claim 3, wherein all the pyrimidine residues are modified to 2'-fluoropyrimidines.

12. The aptamer according to claim 4, wherein all the pyrimidine residues are modified to 2'-fluoropyrimidines.

13. A diagnostic, therapeutic or imaging composition comprising an aptamer as defined in claim 1 with pharmaceutically acceptable carriers and excipients.

14. A composition according to claim 13, which is suitable for the imaging of organs and tissues expressing CA-IX.

15. A composition according to claim 14, wherein said imaging is based on magnetic resonance imaging, positron-emission tomography (PET), computed tomography (CT), ultrasound, photoacoustic imaging (PAI), near-infrared fluorescence (NIRF) or single photon emission computed tomography (SPECT).

16. A diagnostic, therapeutic or imaging composition comprising an aptamer as defined in claim 3 with pharmaceutically acceptable carriers and excipients.

17. A diagnostic, therapeutic or imaging composition comprising an aptamer as defined in claim 4 with pharmaceutically acceptable carriers and excipients.

* * * * *

SEQUENCE LISTING

```
<160> NUMBER OF SEQ ID NOS: 2

<210> SEQ ID NO 1
<211> LENGTH: 24
<212> TYPE: RNA
<213> ORGANISM: Artificial Sequence
<220> FEATURE:
<223> OTHER INFORMATION: synthetic aptamer

<400> SEQUENCE: 1
ucgaaugaac caagguuccu cggc                                          24

<210> SEQ ID NO 2
<211> LENGTH: 25
<212> TYPE: RNA
<213> ORGANISM: Artificial Sequence
<220> FEATURE:
<223> OTHER INFORMATION: synthetic aptamer

<400> SEQUENCE: 2
uucgugccgc ugagugcgua cgggc                                         25
```